United States Patent
Song

(10) Patent No.: US 9,792,515 B2
(45) Date of Patent: Oct. 17, 2017

(54) APPARATUS AND METHOD FOR RECOGNIZING STAMPED CHARACTER AND SYSTEM FOR DETECTING STAMPED DEPTH OF CHARACTER USING THE SAME

(71) Applicant: Hyundai Motor Company, Seoul (KR)

(72) Inventor: Jae Hun Song, Seoul (KR)

(73) Assignee: Hyundai Motor Company, Seoul (KR)

( * ) Notice: Subject to any disclaimer, the term of this patent is extended or adjusted under 35 U.S.C. 154(b) by 886 days.

(21) Appl. No.: 13/959,392

(22) Filed: Aug. 5, 2013

(65) Prior Publication Data

US 2014/0293029 A1 Oct. 2, 2014

(30) Foreign Application Priority Data

Mar. 26, 2013 (KR) ........................ 10-2013-0032024

(51) Int. Cl.
- *H04N 7/18* (2006.01)
- *G06K 9/20* (2006.01)
- *G01N 21/88* (2006.01)
- *G01N 21/89* (2006.01)

(52) U.S. Cl.
CPC ....... *G06K 9/2036* (2013.01); *G01N 21/8806* (2013.01); *G01N 21/8901* (2013.01); *G01N 21/8903* (2013.01); *G01N 2021/8845* (2013.01); *G01N 2021/8918* (2013.01); *G06K 2209/01* (2013.01)

(58) Field of Classification Search
CPC .......... G01N 21/8806; G01N 21/8901; G01N 21/8903; G01N 2021/8918; G01N 2021/8845; G06K 9/2036; G06K 2209/01
See application file for complete search history.

(56) References Cited

U.S. PATENT DOCUMENTS

| | | | |
|---|---|---|---|
| 6,628,808 B1 * | 9/2003 | Bach ...................... | G06K 9/036 235/380 |
| 2010/0103256 A1 * | 4/2010 | Rauber .............. | G01N 21/8806 348/92 |
| 2011/0150346 A1 * | 6/2011 | Panetta .............. | G06K 7/10712 382/218 |

FOREIGN PATENT DOCUMENTS

| | | |
|---|---|---|
| JP | 5-298430 A | 11/1993 |
| JP | 7-44651 A | 2/1995 |
| JP | 7-239907 A | 9/1995 |
| JP | 10-222608 A | 8/1998 |
| JP | 11-281325 A | 10/1999 |
| JP | 3709429 B2 | 8/2005 |
| JP | 2008-58150 A | 3/2008 |
| JP | 2008-64637 A | 3/2008 |
| JP | 2009-58311 A | 3/2009 |
| JP | 2011-21886 A | 2/2011 |
| JP | 2011-227006 A | 11/2011 |

(Continued)

OTHER PUBLICATIONS

Chang et al., "Automatic license plate recognition," in IEEE Transactions on Intelligent Transportation Systems, vol. 5, No. 1, pp. 42-53, Mar. 2004.*

*Primary Examiner* — Joseph Ustaris
*Assistant Examiner* — Jill Sechser
(74) *Attorney, Agent, or Firm* — Morgan, Lewis & Bockius LLP

(57) ABSTRACT

An apparatus and a method recognizes stamped characters, detects stamped depths of characters using the same, and/or accurately recognizes characters even when an image distortion occurs at stamped portion due to different stamped depths of characters.

9 Claims, 13 Drawing Sheets

(56) References Cited

FOREIGN PATENT DOCUMENTS

| | | |
|---|---|---|
| JP | 2012-8843 A | 1/2012 |
| KR | 2003-0018905 A | 3/2003 |
| KR | 10-2009-0021023 A | 2/2009 |
| KR | 10-2010-0013772 A | 2/2010 |
| KR | 10-2010-0014402 A | 2/2010 |
| KR | 10-0955272 B1 | 4/2010 |

\* cited by examiner

APPARATUS AND METHOD FOR RECOGNIZING STAMPED CHARACTER AND SYSTEM FOR DETECTING STAMPED DEPTH OF CHARACTER USING THE SAME

CROSS-REFERENCE TO RELATED APPLICATION

The present application claims priority of Korean Patent Application Number 10-2013-0032024 filed Mar. 26, 2013, the entire contents of which application is incorporated herein for all purposes by this reference.

BACKGROUND OF INVENTION

Field of Invention

The present invention relates to a system and a method for recognizing stamped characters and a system for detecting stamped depths of characters using the same, and more particularly, to a technology of recognizing a stamped vehicle identification number and a technology of detecting stamped depths of stamped characters using the same.

In the present specification, the stamped character means a letter (Hangeul, English, and the like) and a number carved in a solid object, such as metal, in intaglio or relief.

Description of Related Art

Stamping a vehicle identification number (VIN) in a partition wall between an engine room and a driver's seat within a bonnet of a vehicle is required by law.

The vehicle identification number includes an alphabet and a number to indicate a producing country, a manufacturer, a vehicle division, a vehicle model, a detailed vehicle model, a vehicle body shape, a safety device type, displacement, a driver's seat position, a manufactured year, a manufacturing factory, and a producing serial number.

In general, a stamping system is implemented in a robot type that is automatically controlled by a process program and manually controlled by a user and includes a stamped tool (pin) in which a stamped pin is mounted at an end of an arm of the robot.

When a body in white (BIW) that is a workpiece enters a work location, the stamping system determines a position of a vehicle body and a position of the stamped tool, fixes the body in white, and then operates the stamped pin according to a pneumatic control to stamp the vehicle identification number.

Further, the stamping system includes an apparatus for recognizing stamped characters to perform a process of confirming whether the vehicle identification number is accurately stamped.

The apparatus for recognizing stamped characters according to the related art includes two light emitting diode (LED) lighting devices having the same wavelength and one mono camera and uses the two LED lighting devices to irradiate LED lighting to a surface carved with characters at a right angle and then uses the mono camera to photograph the stamped characters. That is, images for the stamped characters are acquired by using a direct irradiation method.

Therefore, when the stamped depths of characters are different due to the wear of the stamped pins, a distorted image occurs at the stamped portions due to scattered reflection and concentration of light caused by a difference in angles of the stamped portions, which leads to the recognition error of the vehicle identification number.

Therefore, even though the stamped pins are worn, a need exists for a method for accurately recognizing stamped characters.

The information disclosed in this Background section is only for enhancement of understanding of the general background of the invention and should not be taken as an acknowledgement or any form of suggestion that this information forms the prior art already known to a person skilled in the art.

BRIEF SUMMARY

Accordingly, various aspects of the present invention have been made to solve the above-mentioned problems occurring in the prior art while advantages achieved by the prior art are maintained intact.

Various aspects of the present invention provide for an apparatus and a method for recognizing stamped characters capable of accurately recognizing characters even when an image distortion occurs at stamped portions due to different stamped depths of characters.

Various aspects of the present invention provide for a system for detecting stamped depths of characters capable of detecting stamped depths of recognized stamped characters.

Various aspects of the present invention provide for an apparatus for recognizing stamped characters, including: a stamped character photographing unit that photographs stamped characters using lighting devices having different wavelengths; an image segmentation unit that segments images photographed by the stamped character photographing unit into each wavelength; an image synthesis unit that synthesizes binarization images for each wavelength segmented by the image segmentation unit; and a recognition control unit that recognizes the stamped characters in the image synthesized by the image synthesis unit Various aspects of the present invention provide for a method for recognizing stamped characters, including: photographing, by a stamped character photographing unit, the stamped characters using lighting devices having different wavelengths; segmenting, by an image segmentation unit, the photographed images into each wavelength; synthesizing, by an image synthesis unit, binarization images for each segmented wavelength; and recognizing, by a recognition control unit, the stamped characters in the synthesized image.

Various aspects of the present invention provide for a system for recognizing stamped characters, including: an apparatus for recognizing stamped characters that segments and synthesizes the stamped characters photographed using lighting devices having different wavelengths into each wavelength; and an apparatus for detecting stamped depths that detects widths of characters recognized by the apparatus for recognizing stamped characters, calculates average values of the detected widths of characters, and detects the stamped depths of characters corresponding to the calculated average values of the widths of characters based on a table in which the stamped depths corresponding to the average values of the widths of stamped characters are written.

The methods and apparatuses of the present invention have other features and advantages which will be apparent from or are set forth in more detail in the accompanying drawings, which are incorporated herein, and the following Detailed Description, which together serve to explain certain principles of the present invention.

DETAILED DESCRIPTION

Reference will now be made in detail to various embodiments of the present invention(s), examples of which are illustrated in the accompanying drawings and described below. While the invention(s) will be described in conjunction with exemplary embodiments, it will be understood that present description is not intended to limit the invention(s) to those exemplary embodiments. On the contrary, the invention(s) is/are intended to cover not only the exemplary embodiments, but also various alternatives, modifications, equivalents and other embodiments, which may be included within the spirit and scope of the invention as defined by the appended claims.

Figure 1:
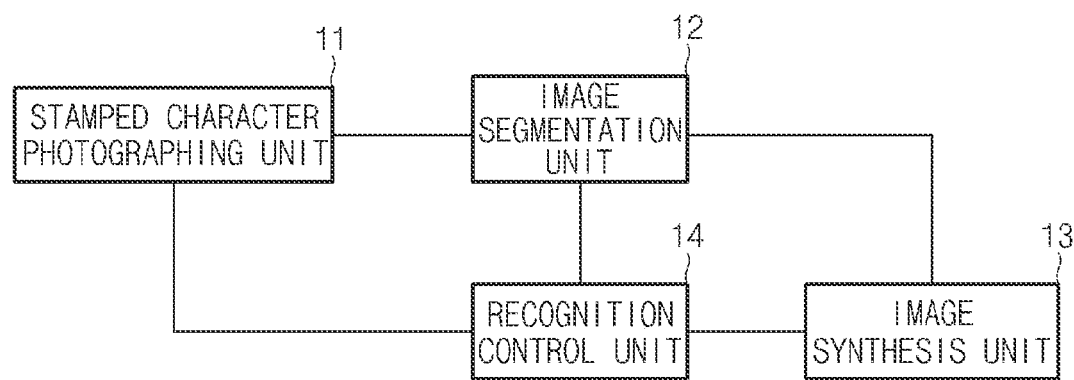
FIG. 1 is a configuration diagram of an exemplary apparatus for recognizing stamped characters according to the present invention.

As illustrated in FIG. 1, the apparatus for recognizing stamped characters according to various embodiments of the present invention may include a stamped character photographing unit 11, an image segmentation unit 12, an image synthesis unit 13, and a recognition control unit 14. The exemplary embodiments of the present invention will describe, for example, an intaglio character as a stamped character.

Describing each component, the stamped character photographing unit 11 photographs the stamped characters using lighting devices having different wavelengths.

Hereinafter, the stamped character photographing unit 11 will be described with reference to FIGS. 2A and 2B.

Figure 2A:
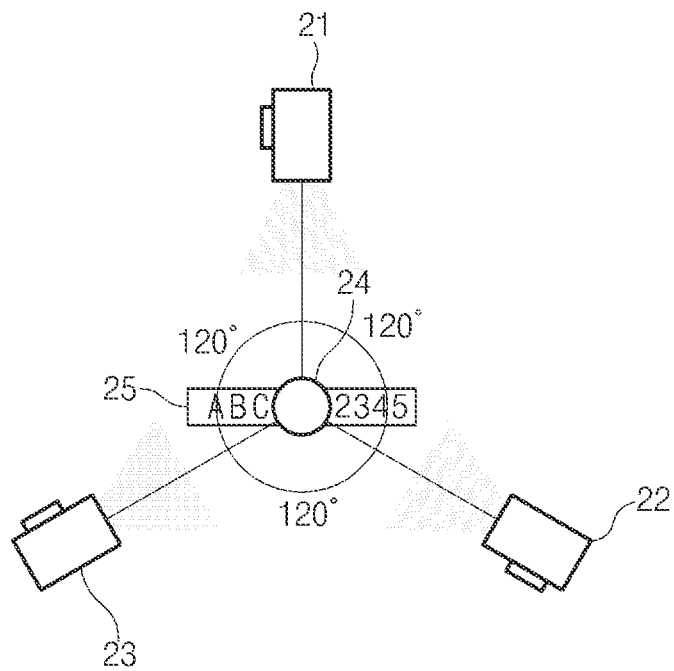
FIGS. 2A and 2B are detailed configuration diagrams of an exemplary stamped character photographing unit according to the present invention.

As illustrated in FIG. 2A, the stamped character photographing unit 11 includes a first lighting device 21 that irradiates light having a red wavelength, a second lighting device 22 that irradiates light having a green wavelength, a third lighting device 23 that irradiates light having a blue wavelength, and a color camera 24.

In this case, the first lighting device 21 is an illuminator in which a plurality of light emitting diodes are arranged and is disposed so that an LED arrangement direction is parallel with a direction of a stamped character string 25.

Further, the second lighting device 22 is disposed at one side at a predetermined angle (for example, 120)° based on the first lighting device 21.

Further, the third lighting device 23 is disposed at the other side at a predetermined angle (for example, 120°) based on the first lighting device 21.

Further, the color camera 24 is disposed at a center of the character string 25 to photograph the stamped characters.

Figure 2B:
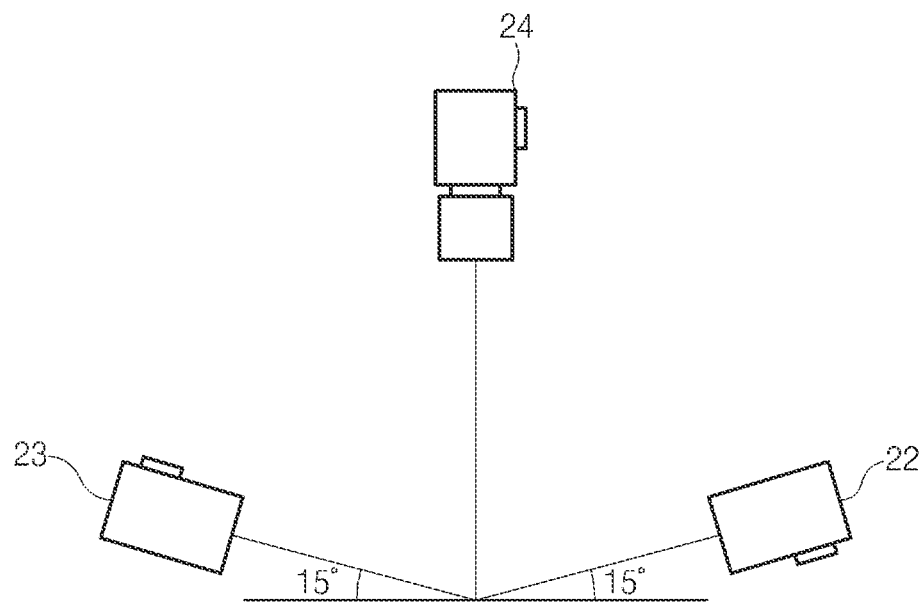

Meanwhile, as illustrated in FIG. 2B, the first lighting device 21, the second lighting device 22, and the third lighting device 23 are disposed at a predetermined angle (for example, 15°) with respect to a surface carved with the character string 25 to irradiate light to the character string 25.

Figure 2C:
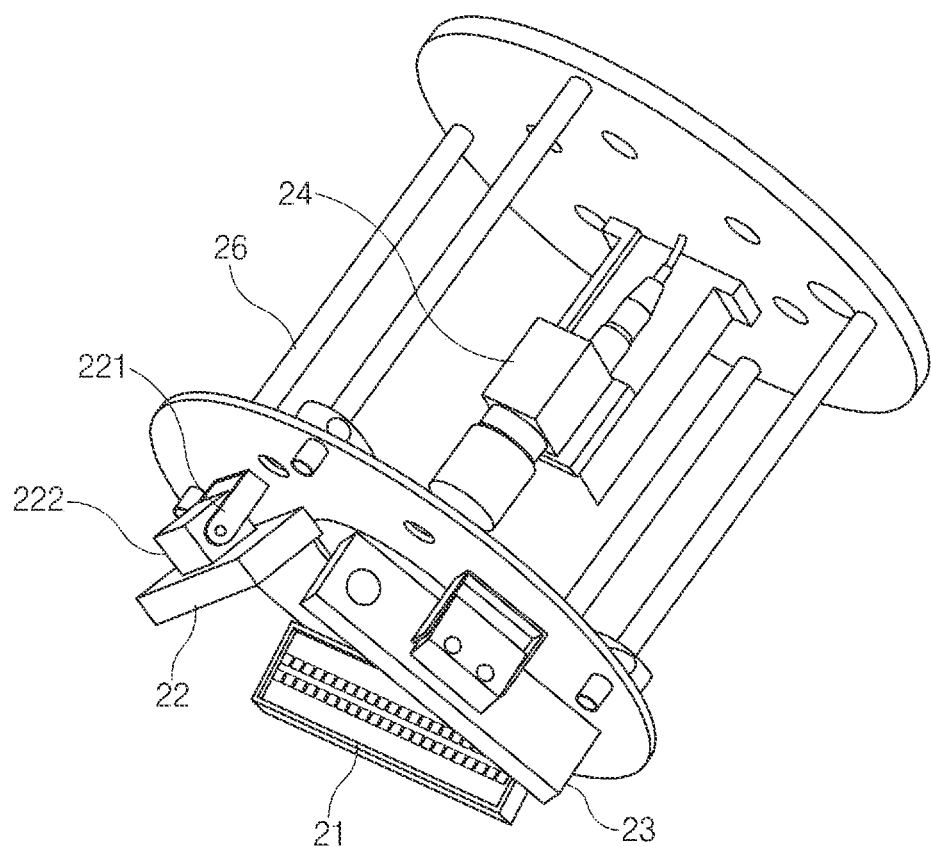
FIG. 2C is a detailed structure diagram of an exemplary stamped character photographing unit according to the present invention.
Figure 2D:
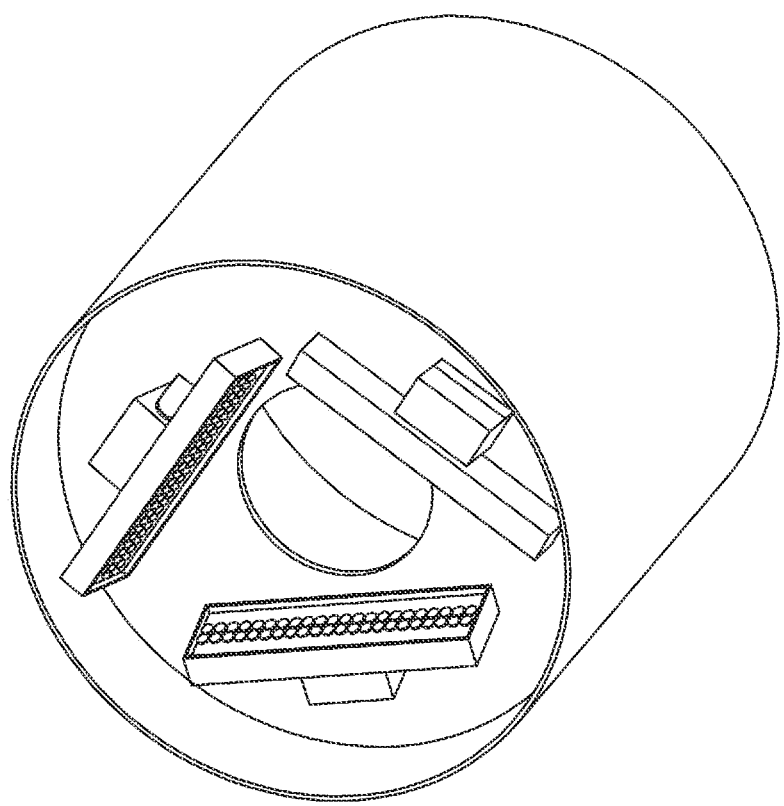
FIG. 2D is an appearance diagram of an exemplary stamped character photographing unit according to the present invention.

A structure of the stamped character photographing unit 11 is as illustrated in FIG. 2C, for example. As illustrated in FIG. 2C, the stamped character photographing unit 11 includes a plurality of distance controllers 26 that control a working distance and the first lighting device 21, the second lighting device 22, and the third lighting device 23 each include an inter-lighting angle controller 221 and an irradiation angle controller 222. Herein, the appearance of the stamped character photographing unit 11 is as illustrated in FIG. 2D.

Next, the image segmentation unit 12 segments images photographed by the stamped character photographing unit 11 for each wavelength. That is, the image segmentation unit 12 segments a binarization image having an R wavelength, a binarization image having a G wavelength, a binarization image having a B wavelength from the images photographed by the stamped character photographing unit 11.

Figure 3A:
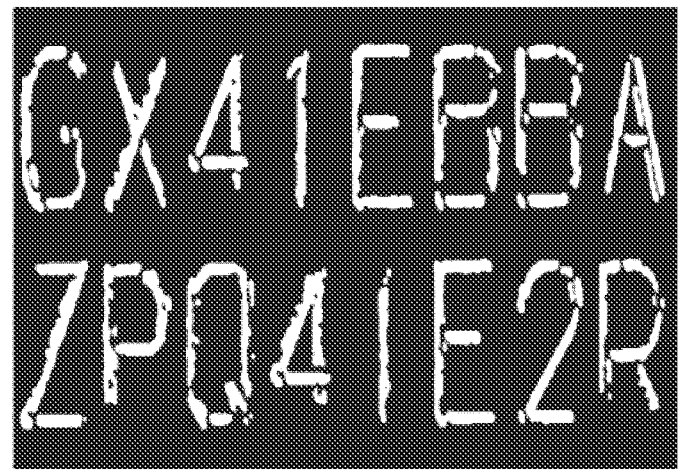
FIGS. 3A, 3B and 3C are exemplary binarization images for each wavelength according to the present invention.
Figure 3B:
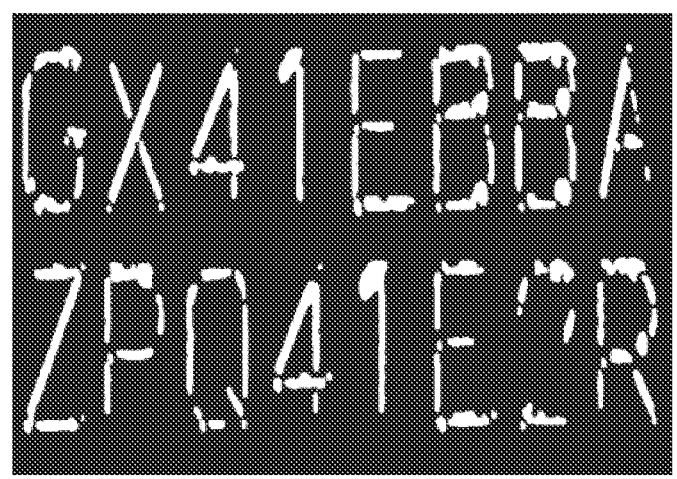
Figure 3C:
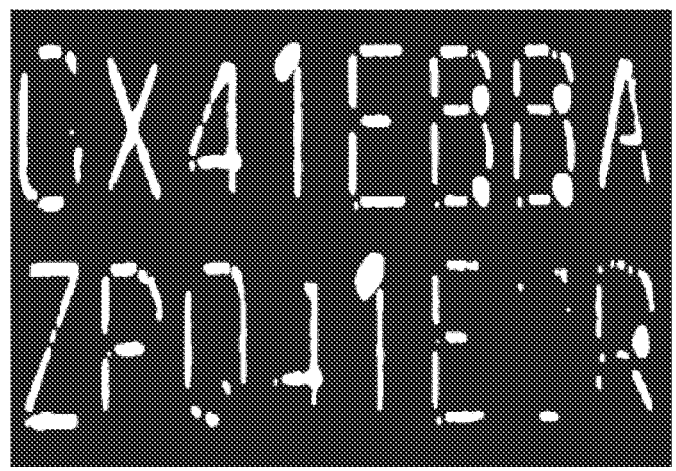

As segmented above, the binarization image having the R wavelength is as illustrated in FIG. 3A and the binarization image having a G wavelength is as illustrated in FIG. 3B, and the binarization image having a B wavelength is as illustrated in FIG. 3C.

It can be appreciated from the binarization images segmented for each wavelength that a distortion of characters due to a wavelength may be changed. For example, in FIG. 3C, a shape number 2 may not substantially be differentiated, but in FIG. 3A, may be fully recognized.

Next, the image synthesis unit 13 synthesizes the binarization image having the R wavelength, the binarization image having the G wavelength, and the binarization image having the B wavelength that are segmented by the image segmentation unit 12.

Figure 4:
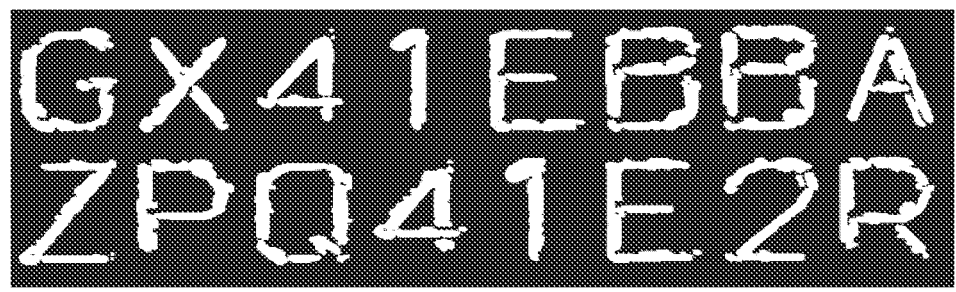
FIG. 4 is diagram illustrating an exemplary synthesized image of the binarization images for each wavelength according to the present invention.

A final image synthesized as above is illustrated in FIG. 4. That is, it can be appreciated from an image obtained by synthesizing the binarization image having the R wavelength, the binarization image having the G wavelength, and the binarization image having the B wavelength that all characters has a perfect shape.

As a result, it can be appreciated that a recognition ratio of stamped characters is increased by using a principle to have the binarization images for each wavelength form a complementary relationship.

Further, the reason for segmenting the binarization image having the R wavelength, the binarization image having the G wavelength, and the binarization image having the B wavelength, respectively, from the images photographed by the stamped character photographing unit 11 and then synthesizing these images is to remove the image distortion occurring due to color blur.

Next, the recognition control unit 14 controls each component to perform their own functions. That is, the recognition control unit 14 controls the stamped character photographing unit 11 to photograph the stamped characters, controls the image segmentation unit 12 to segment the binarization image having the R wavelength, the binarization image having the G wavelength, and the binarization image having the B wavelength from the images photographed by the stamped character photographing unit 11, and controls the image synthesis unit 13 to synthesize the binarization image having the R wavelength, the binarization image having the G wavelength, and the binarization image having the B wavelength that are segmented by the image segmentation unit 12.

In particular, the recognition control unit 14 recognizes the stamped characters in the image synthesized by the image synthesis unit 13.

Figure 5:
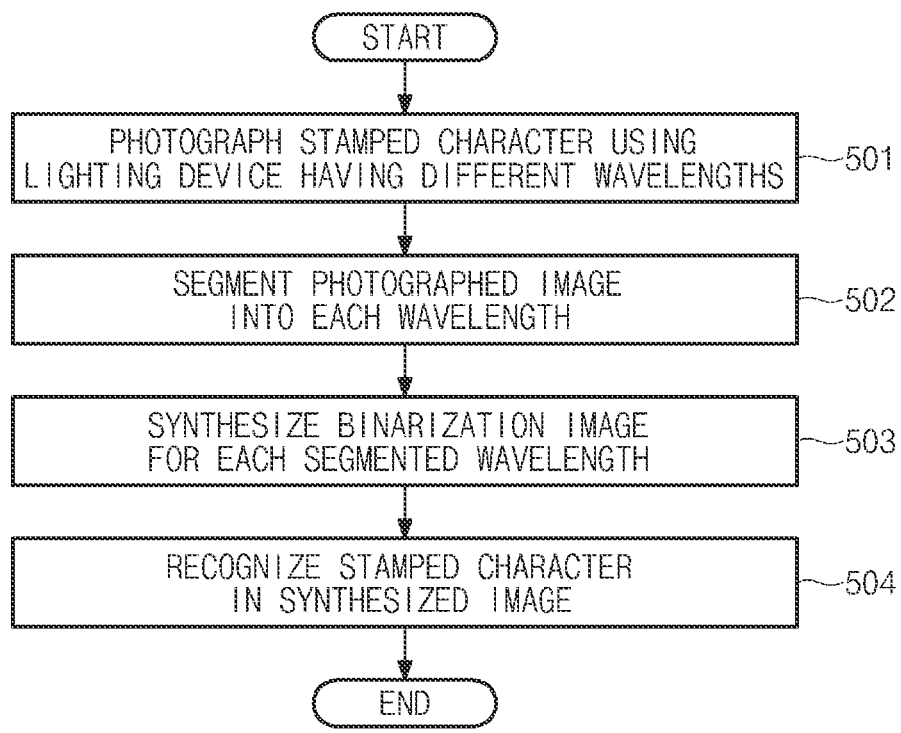
FIG. 5 is a flow chart of an exemplary method for recognizing stamped characters according to the present invention.

FIG. 5 is a flow chart of a method for recognizing stamped characters according to various embodiments of the present invention.

First, the stamped character photographing unit 11 uses lighting devices having different wavelengths to photograph the stamped characters (501). In this case, light having a red wavelength, light having a green wavelength, and light having a blue wavelength are each irradiated.

Next, the image segmentation unit 12 segments images photographed by the stamped character photographing unit 11 into each wavelength (502). In this case, the image segmentation unit 12 segments the binarization image having the R wavelength, the binarization image having the G wavelength, the binarization image having the B wavelength from the image photographed by the stamped character photographing unit 11.

Next, the image synthesis unit 13 synthesizes the binarization images for each wavelength that are segmented by the image segmentation unit 12 (503).

Next, the recognition control unit 14 recognizes the stamped characters in the image synthesized by the image synthesis unit 13 (504).

Hereinafter, a technology of detecting the stamped depths will be described based on the stamped characters recognized by the stamped character recognition technology as described above.

Figure 6:
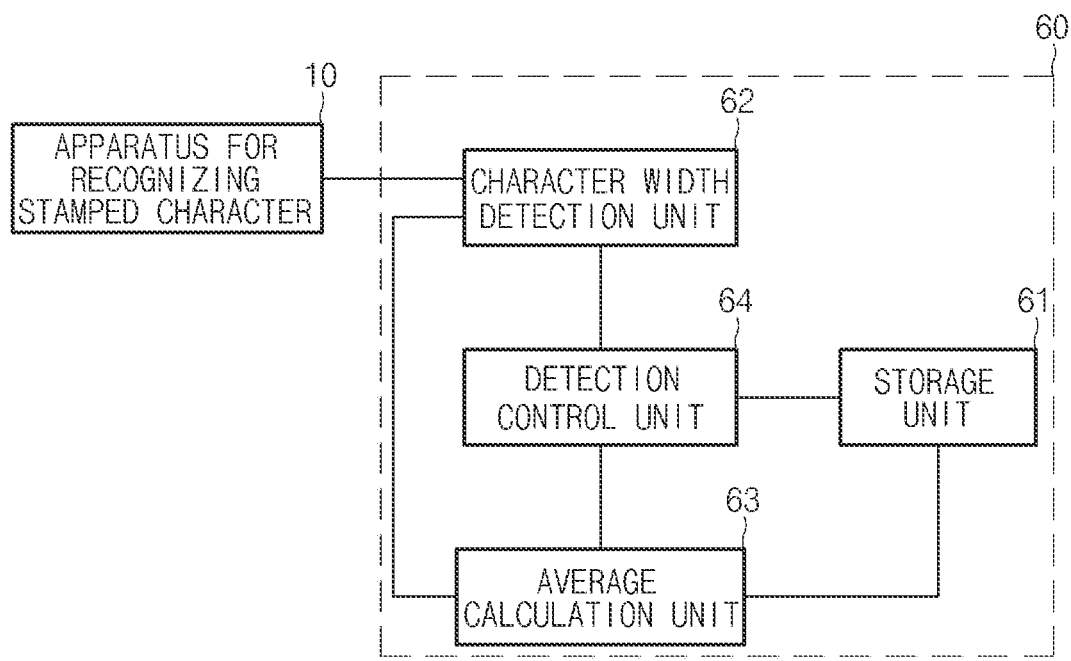
FIG. 6 is a configuration diagram of an exemplary system for detecting stamped depths of characters according to the present invention.

FIG. 6 is a configuration diagram of a system for detecting stamped depths of characters according to various embodiments of the present invention.

As illustrated in FIG. 6, a system for detecting stamped depths according to various embodiments of the present invention may include an apparatus 10 for recognizing stamped characters and an apparatus 60 for detecting stamped depths. In this configuration, the apparatus for detecting stamped depths 60 may include a storage unit 61, a character width detection unit 62, an average value calculation unit 63, and a detection control unit 64.

In this configuration, the apparatus 10 for recognizing stamped characters performs a function as described in FIGS. 1 to 5 and the apparatus 60 for detecting stamped depths detects the widths of characters recognized by the apparatus 10 for recognizing stamped characters, calculates average values of the widths of the detected characters, and detects the stamped depths of characters corresponding to the average value of the widths of the calculated characters based on a table in which the stamped depths corresponding to the average values of the widths of stamped characters are written.

Figure 7:
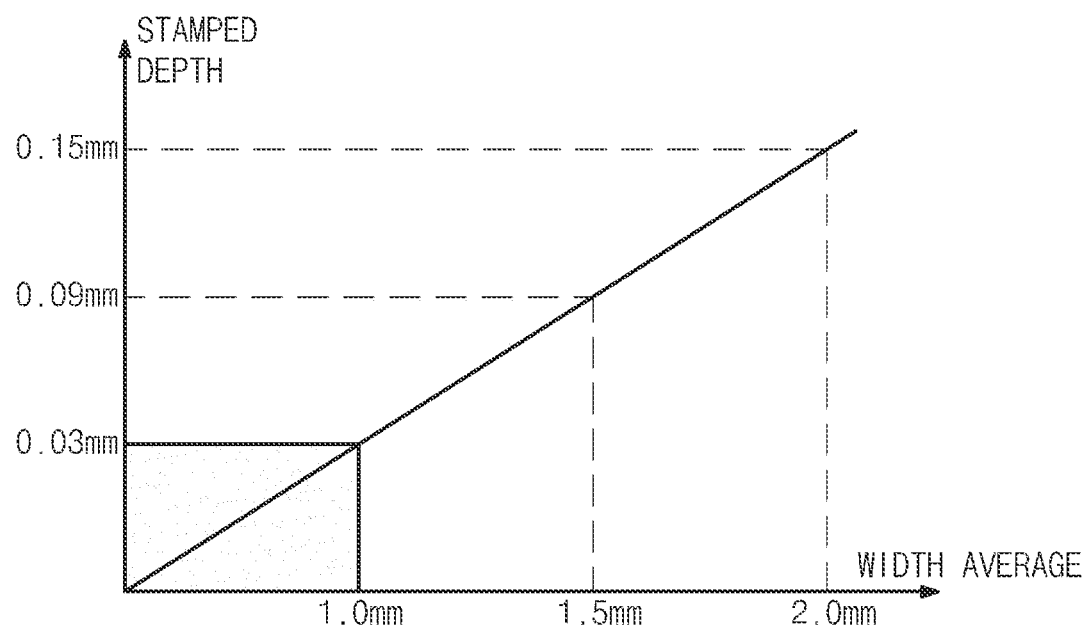
FIG. 7 is an exemplified diagram of a table in which stamped depths corresponding to average values of widths of stamped characters are written, according to the present invention.

Next, describing each component of the apparatus 60 for detecting stamped depths, first, the storage unit 61 first stores the table in which the stamped depths corresponding to the average values of the widths of stamped characters are written. For example, as illustrated in FIG. 7, the storage unit 61 includes a table having a graph form.

Next, the character width detection unit 62 uses a filter having a grating form to detect the widths of characters recognized by the apparatus for recognizing stamped characters. In this case, the widths may be calculated by selecting characters that are located at a position at which the lighting devices of each wavelength is evenly irradiated, that is, a center of the character string. For example, if the character string is ABCDEFGHI, E is selected.

This will be described with reference to FIGS. 8A to 8C.

Figure 8A:
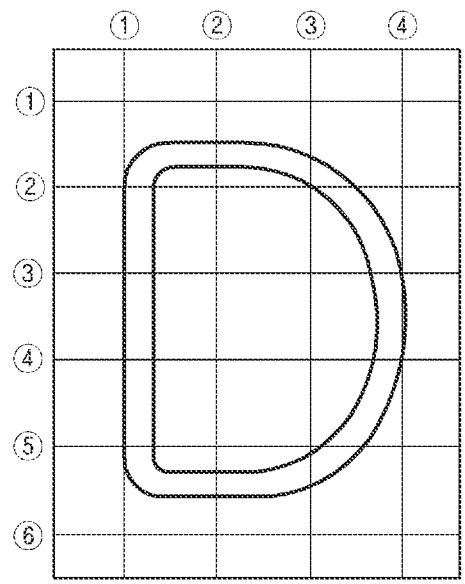
FIGS. 8A, 8B and 8C are an exemplified diagram of an exemplary process of detecting the widths of characters using a grating filter according to the present invention.
Figure 8B:
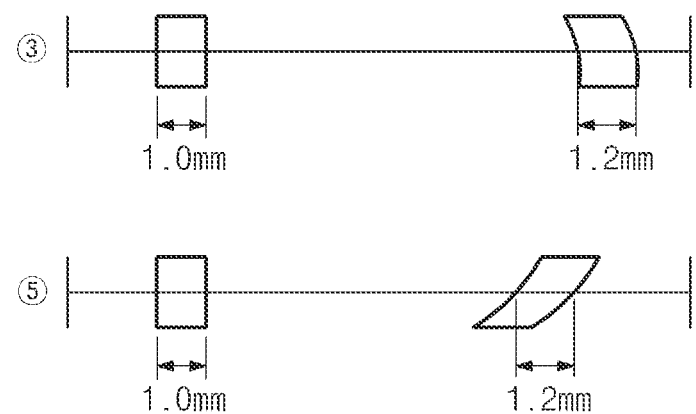
Figure 8C:
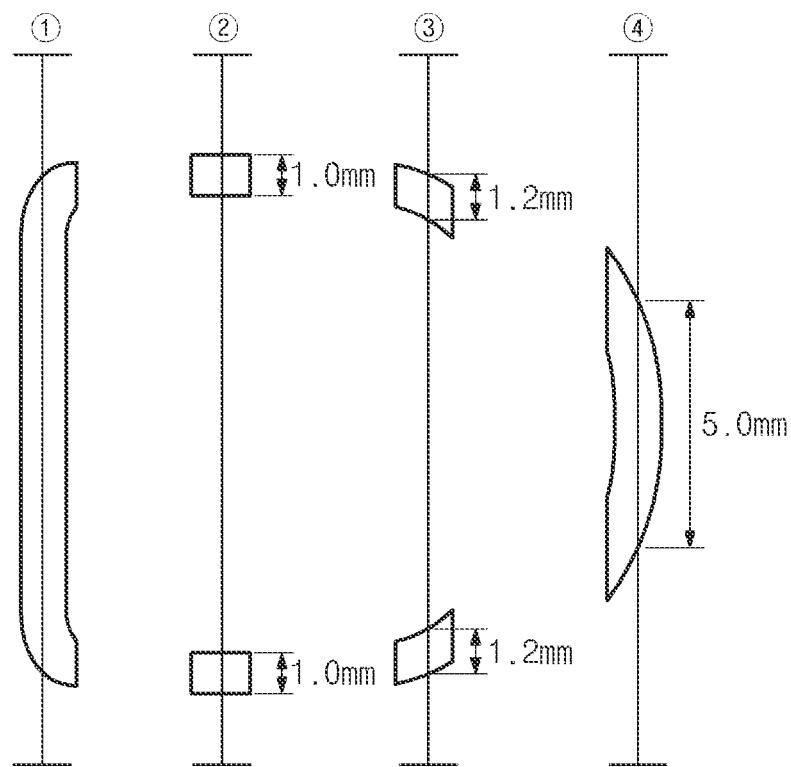

FIGS. 8A to 8C are an exemplified diagram of a process of detecting widths of characters using the grating filter according to various embodiments of the present invention and FIG. 8A illustrates a state in which a filter having horizontal 4-line and vertical 6-line is applied to alphabet 'D'.

As illustrated in FIG. 8A, the horizontal line of the filter contacting the alphabet 'D' is ②, ③, ④, and ⑤ and the vertical line contacting the alphabet 'D' is ①, ②, ③, ④. In this case, the widths of the alphabet 'D' are detected in all the lines of the filter that contact the alphabet 'D'.

FIG. 8B illustrates a process of calculating, for example, the widths of the alphabet 'D" in the lines ③ and ⑤ among the horizontal lines ②, ③, ④, and ⑤ of the filter contacting the alphabet 'D'.

As illustrated in FIG. 8B, for example, a width of a straight line of the alphabet 'D' is 1.0 mm and a width of a curved line thereof is 1.2 mm. Since the horizontal lines ② and ④ of the filter are the same, the width of the alphabet 'D' calculated in association with the horizontal line becomes eight in total.

FIG. 8C illustrates a process of calculating the widths of the alphabet 'D' in the vertical lines ①, ②, ③, and ④ of the filter contacting the alphabet 'D'.

As illustrated in FIG. 8C, the widths of the alphabet D in the lines ① and ④ among the vertical lines ①, ②, ③, and ④ of the filter are a value exceeding a maximum threshold value (for example, 2.0 mm), which is deleted by being considered as an invalid value. To the contrary, a value that does not exceed a minimum threshold value (0.2 mm) is deleted by being considered as a noise.

The widths of the alphabet 'D' in the line ② each are 1.0 mm and the widths of the alphabet 'D' in the line ③ each are 1.2 mm.

Therefore, the width of the alphabet 'D' calculated in association with the vertical line becomes four in total (two of 1.0 mm and two of 1.2 mm).

As a result, the number of widths of the alphabet 'D' calculated by being associated with a 6×4 grating filter becomes 12 in total.

Next, the average calculation unit 63 arranges the widths of characters detected by the character width detection unit 62 in an ascending order and then extracts a predetermined number (for example, six) and calculates the average thereof. In this case, the extracted value may be a value located in a center of the arrangement.

In the foregoing example, the arrangement becomes 1, 1, 1, 1, 1, 1, 1.2, 1.2, 1.2, 1.2, 1.2, and 1.2 and the extracted value becomes 1, 1, 1, 1.2, 1.2, and 1.2.

Therefore, the average value calculated by the average calculation unit 63 becomes 1.1.

Next, the detection control unit 64 controls each component to perform their own functions. That is, the detection control unit 64 controls the storage unit 61 to store the table in which the stamped depths corresponding to the average values of the widths of stamped characters are written, controls the character width detection unit 62 to select the optimal detection character from the character string and calculate the selected widths of characters, and controls the average calculation unit 63 to calculate the average of the widths of characters detected by the character width detection unit 62.

In particular, the detection control unit 64 detects the stamped depths of characters corresponding to the average values of the widths of characters calculated by the average calculation unit 63, based on the table stored in the storage unit 61.

Figure 9:
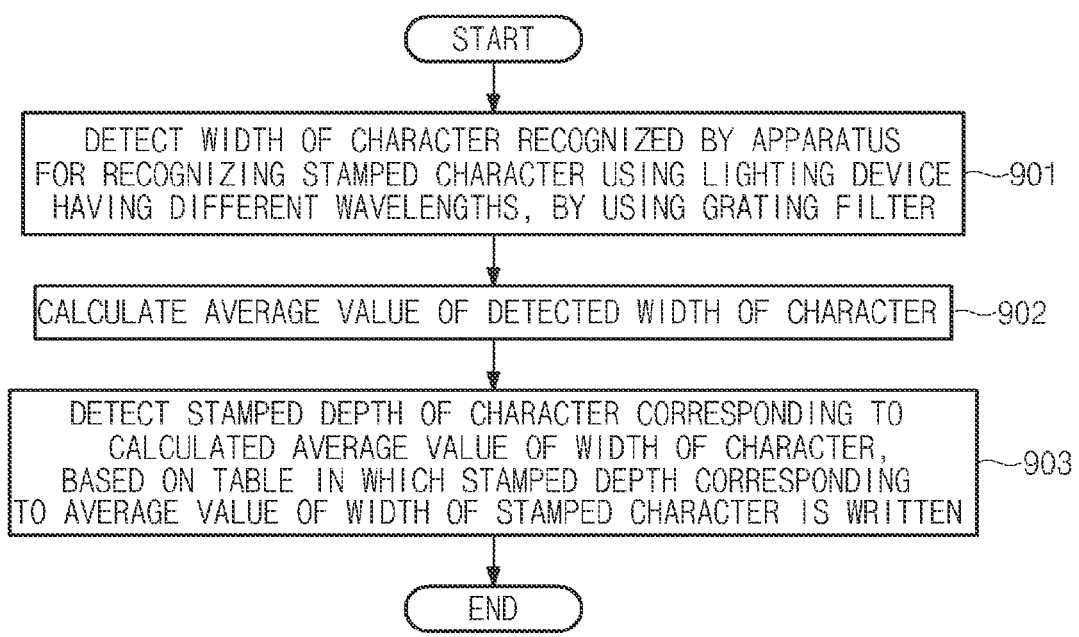
FIG. 9 is a flow chart of an exemplary method for detecting stamped depths of characters according to the present invention.

FIG. 9 is a flow chart of a method for detecting stamped depths of characters according to various embodiments of the present invention.

First, the character width detection unit 62 detects the widths of characters recognized by the apparatus for recognizing stamped characters (hereinafter, a stamped character recognition apparatus) using the lighting devices having different wavelengths, by using the grating filter (901).

Next, the average calculation unit 63 calculates the average values of the widths of characters detected by the character width detection unit 62 (902).

Next, the detection control unit 64 detects the stamped depths of characters corresponding to the average values of the widths of characters calculated by the average calculation unit 63, based on the table in which the stamped depths corresponding to the average values of the widths of stamped characters are written (903).

As set forth above, according to various embodiments of the present invention, even when the stamped depths of characters are different, it is possible to accurately recognize the stamped characters.

Further, according to various embodiments of the present invention, it is possible to detect the stamped depths of stamped characters based on the widths of stamped characters.

In addition, according to various embodiments of the present invention, it is possible to provide the wear information of the stamped pins by detecting the stamped depths of stamped characters based on the widths of stamped characters.

The foregoing descriptions of specific exemplary embodiments of the present invention have been presented for purposes of illustration and description. They are not intended to be exhaustive or to limit the invention to the precise forms disclosed, and obviously many modifications and variations are possible in light of the above teachings. The exemplary embodiments were chosen and described in order to explain certain principles of the invention and their practical application, to thereby enable others skilled in the art to make and utilize various exemplary embodiments of the present invention, as well as various alternatives and modifications thereof. It is intended that the scope of the invention be defined by the Claims appended hereto and their equivalents.

What is claimed is:

1. A system for detecting intaglio characters, comprising:
   an apparatus for recognizing intaglio characters that segments and synthesizes the intaglio characters photographed using lighting devices having different wavelengths into each wavelength; and
   an apparatus for detecting intaglio depths that detects widths of characters recognized by the apparatus for recognizing intaglio characters, calculates average values of the detected widths of characters, and detects the intaglio depths of characters corresponding to the calculated average values of the widths of characters based on a table in which the intaglio depths corresponding to the average values of the widths of intaglio characters are written,
   wherein each of the intaglio depths is a depth below a surface of a top surface of each of the intaglio characters.

2. The system of claim 1, wherein the apparatus for detecting intaglio depths selects a character located at a center of a character string recognized by the apparatus for recognizing intaglio characters.

3. The system of claim 1, wherein the apparatus for detecting intaglio depths deletes widths of characters that are not included in a threshold range.

4. The system of claim 3, wherein the apparatus for detecting intaglio depths arranges the widths of characters in an ascending order, extracts a predetermined number, and calculates an average thereof.

5. The system of claim 4, wherein the apparatus for detecting intaglio depths extracts a value located at the center of the arrangement according to priority, at the time of extracting the predetermined number.

6. The system of claim 1, wherein the apparatus for recognizing intaglio characters configured to:
   photograph the intaglio characters using lighting devices having different wavelengths;
   segment images into each wavelength;
   synthesize binarization images for each wavelength; and
   recognize the intaglio characters in the image.

7. The system of claim 6, wherein the apparatus for recognizing intaglio characters includes:
   a first lighting device that irradiates light having a red wavelength based on a plurality of arranged LEDs;
   a second lighting device that irradiates light having a green wavelength;
   a third lighting device that irradiates light having a blue wavelength; and
   a color camera that photographs the intaglio characters.

8. The system of claim 6, wherein the apparatus for recognizing intaglio characters segments a binarization image having an R wavelength, a binarization image having a G wavelength, a binarization image having a B wavelength, respectively, from the images.

9. A system for detecting intaglio characters, comprising:
   a color camera that photographs the intaglio characters using lighting devices having different wavelengths,
   wherein a system for detecting intaglio depths of characters segments and synthesizes the intaglio characters photographed by a color camera into each wavelength to recognize the intaglio characters and detects widths of the intaglio characters, calculates average values of the detected widths of characters, and detects the intaglio depths of characters corresponding to the calculated average values of the widths of characters based on a table in which the intaglio depths corresponding to the average values of the widths of intaglio characters are written,
   wherein each of the intaglio depths is a depth below a surface of a top surface of each of the intaglio characters.

* * * * *